(12) United States Patent
Shiu et al.

(10) Patent No.: US 9,375,276 B2
(45) Date of Patent: *Jun. 28, 2016

(54) MICROWAVE ANTENNA HAVING A REACTIVELY-LOADED LOOP CONFIGURATION

(71) Applicant: COVIDIEN LP, Mansfield, MA (US)

(72) Inventors: Brian Shiu, Sunnyvale, CA (US);
Joseph D. Brannan, Erie, CO (US);
Mani N. Prakash, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 224 days.

This patent is subject to a terminal disclaimer.

(21) Appl. No.: 14/189,769

(22) Filed: Feb. 25, 2014

(65) Prior Publication Data
US 2014/0180269 A1    Jun. 26, 2014

Related U.S. Application Data

(63) Continuation of application No. 12/826,902, filed on Jun. 30, 2010, now Pat. No. 8,672,933.

(51) Int. Cl.
*A61B 18/18* (2006.01)
*A61B 18/00* (2006.01)

(52) U.S. Cl.
CPC ..... *A61B 18/1815* (2013.01); *A61B 2018/0013* (2013.01); *A61B 2018/1846* (2013.01); *A61B 2018/1869* (2013.01)

(58) Field of Classification Search
CPC ............... A61B 2018/1846; A61B 18/1815; A61N 1/40
USPC ................................ 606/33, 41; 607/154–156
See application file for complete search history.

(56) References Cited

U.S. PATENT DOCUMENTS

| D263,020 S | 2/1982 | Rau, III |
| D295,893 S | 5/1988 | Sharkany et al. |

(Continued)

FOREIGN PATENT DOCUMENTS

| CN | 1103807 A | 6/1995 |
| DE | 390937 C | 3/1924 |

(Continued)

OTHER PUBLICATIONS

Alexander et al., "Magnetic Resonance Image-Directed Stereotactic Neurosurgery: Use of Image Fusion with Computerized Tomography to EnhanceSpatial Accuracy" Journal Neurosurgery, 83 (1995), pp. 271-276.

(Continued)

*Primary Examiner* — Jocelyn D Ram

(57) ABSTRACT

A microwave ablation system is provided. The microwave ablation system includes a power source. A microwave antenna is adapted to connect to the power source via a coaxial cable feed including an inner conductor defining a portion of a radiating section of the microwave antenna, an outer conductor and dielectric shielding. The inner conductor loops back around and toward the outer conductor of the coaxial cable feed such that a distal end of the inner conductor is operably disposed adjacent the dielectric shielding. The inner conductor includes one or more reactive components disposed thereon forming a reactively-loaded loop configuration configured to maximize delivery of microwave energy from the power source to tissue such that a desired effect to tissue is achieved.

14 Claims, 6 Drawing Sheets

(56) References Cited

U.S. PATENT DOCUMENTS

| | | | |
|---|---|---|---|
| D295,894 S | 5/1988 | Sharkany et al. | |
| 5,186,181 A | 2/1993 | Franconi et al. | |
| 5,370,644 A | 12/1994 | Langberg | |
| 5,370,677 A | 12/1994 | Rudie et al. | |
| 5,441,499 A | 8/1995 | Fritzsch | |
| 5,620,480 A | 4/1997 | Rudie | |
| 5,683,382 A | 11/1997 | Lenihan et al. | |
| 5,755,754 A | 5/1998 | Rudie et al. | |
| 5,800,494 A * | 9/1998 | Campbell | A61B 18/18 606/33 |
| 5,916,240 A | 6/1999 | Rudie et al. | |
| 5,916,241 A | 6/1999 | Rudie et al. | |
| 6,016,811 A | 1/2000 | Knopp et al. | |
| 6,032,078 A | 2/2000 | Rudie | |
| D424,694 S | 5/2000 | Tetzlaff et al. | |
| D425,201 S | 5/2000 | Tetzlaff et al. | |
| 6,097,985 A | 8/2000 | Kasevich et al. | |
| 6,181,970 B1 | 1/2001 | Kasevich | |
| 6,190,382 B1 | 2/2001 | Ormsby et al. | |
| 6,233,490 B1 | 5/2001 | Kasevich | |
| 6,245,062 B1 * | 6/2001 | Berube | A61B 18/14 606/33 |
| 6,287,302 B1 * | 9/2001 | Berube | A61B 18/1815 606/33 |
| D449,886 S | 10/2001 | Tetzlaff et al. | |
| 6,366,818 B1 | 4/2002 | Bolmsjo | |
| D457,958 S | 5/2002 | Dycus et al. | |
| D457,959 S | 5/2002 | Tetzlaff et al. | |
| 6,424,869 B1 | 7/2002 | Carr et al. | |
| 6,471,696 B1 * | 10/2002 | Berube | A61B 18/1492 606/33 |
| 6,635,055 B1 | 10/2003 | Cronin | |
| 6,673,068 B1 * | 1/2004 | Berube | A61B 5/042 600/374 |
| 6,699,241 B2 | 3/2004 | Rappaport et al. | |
| D496,997 S | 10/2004 | Dycus et al. | |
| D499,181 S | 11/2004 | Dycus et al. | |
| 7,004,938 B2 | 2/2006 | Ormsby et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| 7,197,363 B2 | 3/2007 | Prakash et al. | |
| D541,418 S | 4/2007 | Schechter et al. | |
| D541,938 S | 5/2007 | Kerr et al | |
| 7,311,702 B2 | 12/2007 | Tallarida et al. | |
| D564,662 S | 3/2008 | Moses et al. | |
| 7,594,913 B2 | 9/2009 | Ormsby et al. | |
| D613,412 S | 4/2010 | DeCarlo | |
| 7,863,984 B1 | 1/2011 | Behnke | |
| 7,963,785 B2 | 6/2011 | Arts et al. | |
| 8,038,693 B2 | 10/2011 | Allen | |
| 8,069,553 B2 | 12/2011 | Bonn | |
| 8,118,808 B2 | 2/2012 | Smith et al. | |
| 8,188,435 B2 | 5/2012 | Podhajsky et al. | |
| 8,197,473 B2 | 6/2012 | Rossetto et al. | |
| 8,202,270 B2 | 6/2012 | Rossetto et al. | |
| 8,216,227 B2 | 7/2012 | Podhajsky | |
| 8,235,981 B2 | 8/2012 | Prakash et al. | |
| 8,282,632 B2 | 10/2012 | Rossetto | |
| 8,292,881 B2 | 10/2012 | Brannan et al. | |
| 8,313,486 B2 | 11/2012 | Kim et al. | |
| 8,409,188 B2 | 4/2013 | Kim et al. | |
| 8,469,953 B2 | 6/2013 | DeCarlo | |
| 8,491,579 B2 | 7/2013 | Rossetto | |
| 8,672,933 B2 | 3/2014 | Shiu et al. | |
| 8,728,067 B2 * | 5/2014 | Prakash | A61B 5/0422 606/33 |
| 8,968,287 B2 * | 3/2015 | Shroff | A61B 18/18 606/33 |
| 2002/0115986 A1 | 8/2002 | Shadduck | |
| 2002/0193783 A1 * | 12/2002 | Gauthier | A61B 18/1492 606/17 |
| 2003/0195433 A1 | 10/2003 | Turovskiy et al. | |
| 2003/0195499 A1 | 10/2003 | Prakash et al. | |
| 2004/0106917 A1 | 6/2004 | Ormsby et al. | |
| 2007/0198006 A1 | 8/2007 | Prakash et al. | |
| 2007/0233057 A1 | 10/2007 | Konishi | |
| 2009/0125091 A1 | 5/2009 | Schoenbach et al. | |
| 2010/0045559 A1 | 2/2010 | Rossetto | |
| 2010/0256624 A1 | 10/2010 | Brannan et al. | |
| 2010/0262134 A1 | 10/2010 | Jensen et al. | |
| 2010/0268223 A1 | 10/2010 | Coe et al. | |
| 2010/0268225 A1 | 10/2010 | Coe et al. | |
| 2010/0286681 A1 | 11/2010 | Podhajsky | |
| 2010/0286683 A1 | 11/2010 | Podhajsky | |
| 2010/0305560 A1 | 12/2010 | Peterson | |
| 2010/0321192 A1 | 12/2010 | Brannan | |
| 2010/0321257 A1 | 12/2010 | Brannan | |
| 2010/0331834 A1 | 12/2010 | Peterson et al. | |
| 2011/0034913 A1 | 2/2011 | Brannan | |
| 2011/0034917 A1 | 2/2011 | Brannan | |
| 2011/0034919 A1 | 2/2011 | DeCarlo | |
| 2011/0040300 A1 * | 2/2011 | Brannan | A61B 18/18 606/41 |
| 2011/0054458 A1 | 3/2011 | Behnke | |
| 2011/0054459 A1 | 3/2011 | Peterson | |
| 2011/0060325 A1 | 3/2011 | Bonn | |
| 2011/0060326 A1 | 3/2011 | Smith et al. | |
| 2011/0071511 A1 | 3/2011 | Brannan et al. | |
| 2011/0071512 A1 | 3/2011 | Behnke, II et al. | |
| 2011/0071582 A1 | 3/2011 | Willyard et al. | |
| 2011/0073594 A1 | 3/2011 | Bonn | |
| 2011/0077633 A1 * | 3/2011 | Bonn | A61B 18/1815 606/33 |
| 2011/0077634 A1 * | 3/2011 | Brannan | A61B 18/18 606/33 |
| 2011/0077635 A1 | 3/2011 | Bonn | |
| 2011/0077636 A1 | 3/2011 | Brannan et al. | |
| 2011/0077637 A1 | 3/2011 | Brannan | |
| 2011/0077638 A1 | 3/2011 | Brannan | |
| 2011/0077639 A1 | 3/2011 | Brannan et al. | |
| 2011/0098695 A1 | 4/2011 | Brannan | |
| 2011/0098696 A1 | 4/2011 | Brannan | |
| 2011/0098697 A1 | 4/2011 | Brannan | |
| 2011/0118721 A1 | 5/2011 | Brannan | |
| 2011/0118731 A1 | 5/2011 | Ladtkow | |
| 2011/0172659 A1 | 7/2011 | Brannan | |
| 2011/0184403 A1 | 7/2011 | Brannan | |
| 2011/0190754 A1 | 8/2011 | Kim et al. | |
| 2011/0208177 A1 | 8/2011 | Brannan | |
| 2011/0208179 A1 | 8/2011 | Prakash et al. | |
| 2011/0208180 A1 | 8/2011 | Brannan | |
| 2011/0208184 A1 | 8/2011 | Brannan | |
| 2011/0213351 A1 | 9/2011 | Lee et al. | |
| 2011/0213352 A1 | 9/2011 | Lee et al. | |
| 2011/0213353 A1 | 9/2011 | Lee et al. | |
| 2011/0224504 A1 | 9/2011 | Ladtkow et al. | |
| 2011/0238053 A1 * | 9/2011 | Brannan | A61B 17/3211 606/33 |
| 2011/0238055 A1 | 9/2011 | Kim et al. | |
| 2011/0270240 A1 | 11/2011 | Shiu et al. | |
| 2011/0282336 A1 | 11/2011 | Brannan et al. | |
| 2011/0295245 A1 | 12/2011 | Willyard et al. | |
| 2011/0295246 A1 | 12/2011 | Prakash et al. | |
| 2011/0299719 A1 | 12/2011 | Podhajsky et al. | |
| 2011/0301589 A1 | 12/2011 | Podhajsky et al. | |
| 2011/0301590 A1 | 12/2011 | Podhajsky et al. | |
| 2011/0301591 A1 | 12/2011 | Podhajsky et al. | |
| 2011/0319880 A1 | 12/2011 | Prakash et al. | |
| 2012/0004651 A1 | 1/2012 | Shiu et al. | |

FOREIGN PATENT DOCUMENTS

| | | |
|---|---|---|
| DE | 1099658 | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |

(56) References Cited

FOREIGN PATENT DOCUMENTS

| | | |
|---|---|---|
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 836 868 A2 | 4/1998 |
| EP | 0 882 955 A1 | 12/1998 |
| EP | 1 159 926 A2 | 12/2001 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| JP | 2001231870 A | 8/2001 |
| JP | 2008142467 A | 6/2008 |
| SU | 166452 | 11/1964 |
| SU | 401367 A1 | 10/1973 |
| SU | 727201 A2 | 4/1980 |
| WO | 03/088858 A1 | 10/2003 |
| WO | 2010/035831 A1 | 4/2010 |

OTHER PUBLICATIONS

Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.

(56) References Cited

OTHER PUBLICATIONS

E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure. TM. Vessel Sealing System: A Case Report" Innovations That Work, Feb. 2002.
Humphries Jr. et al., "Finite.cndot.Element Codes to Model Electrical Heating and Non.cndot.Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents". Pediatric Endosurgery & Innovative Techniques, vol. 6, No. 1, 2002.
European Search Report EP 09010873.9 extended dated Nov. 13, 2009.
European Search Report EP 09010877.0 extended dated Dec. 3, 2009.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10158944.8 extended dated Jun. 21, 2010.
European Search Report EP 10161722.3 extended dated Jun. 16, 2010.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
U.S. Appl. No. 08/136,098, filed Oct. 14, 1993, Roger A. Stern.
U.S. Appl. No. 08/483,742, filed Jun. 7, 1995, Roger A. Stern.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.

(56) References Cited

OTHER PUBLICATIONS

European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.

LigaSure.TM. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure.TM. Vessel Sealing System and LigaSure.TM. Atlas 20 cm Open Instrument" Innovations That Work, Jun. 2003.
Muller et al., "Extended Left Hemicolectomy Using the LigaSure.TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . ." Journal of Applied Sciences. cndot.Yingyong Kexue Xuebao, Shangha CN, vol. 23, No. 2:(Mar. 2005); pp. 160-184, Abstract only.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/1977).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.

(56) References Cited

OTHER PUBLICATIONS

Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.cndot.825.
Urologix, Inc.—Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.

\* cited by examiner

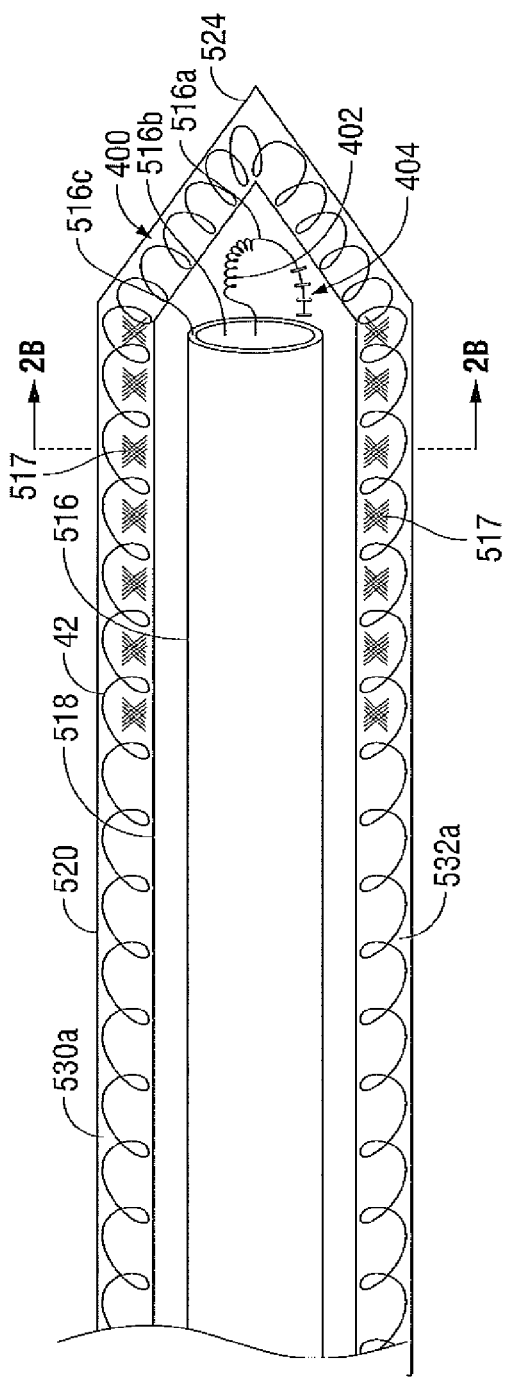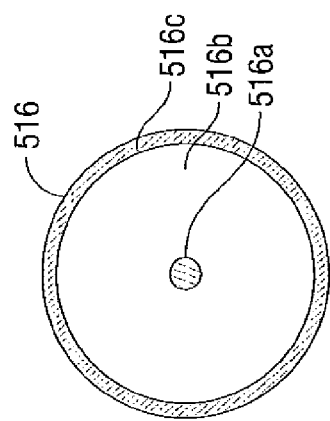
FIG. 2A
FIG. 2B

MICROWAVE ANTENNA HAVING A REACTIVELY-LOADED LOOP CONFIGURATION

CROSS-REFERENCE TO RELATED APPLICATIONS

The present application is a continuation application of U.S. patent application Ser. No. 12/826,902 filed on Jun. 30, 2010, the entire contents of which are incorporated by reference herein.

BACKGROUND

1. Technical Field

The present disclosure relates to microwave antennas. More particularly, the present disclosure relates to microwave antennas having a reactively-loaded loop configuration defining a portion of a radiating section of the microwave antenna.

2. Background of Related Art

Microwave ablation procedures, e.g., such as those performed for menorrhagia, are typically done to ablate the targeted tissue to denature or kill the tissue. Many procedures and types of devices utilizing electromagnetic radiation therapy are known in the art. Such microwave therapy is typically used in the treatment of tissue and organs such as the prostate, heart, and liver.

One non-invasive procedure generally involves the treatment of tissue (e.g., a tumor) underlying the skin via the use of microwave energy. The microwave energy is able to non-invasively penetrate the skin to reach the underlying tissue. Typically, microwave energy is generated by a power source, e.g., microwave generator, and transmitted to tissue via a microwave antenna that is fed with a coaxial cable that operably couples to a radiating section of the microwave antenna.

For optimal energy delivery efficiency from the microwave generator to the microwave antenna, impedance associated with the coaxial cable, the radiating section and/or tissue need to equal to one another, i.e., an impedance match between the coaxial cable, the radiating section and/or tissue. In certain instances, an impedance mismatch may be present between the coaxial cable, the radiating section and/or tissue, and the energy delivery efficiency from the microwave generator to the microwave antenna is compromised, e.g., decreased, which, in turn, may compromise a desired effect to tissue, e.g., ablation to tissue.

SUMMARY

The present disclosure provides a microwave ablation system. The microwave ablation system includes a power source. A microwave antenna is adapted to connect to the power source via a coaxial cable feed including an inner conductor defining a portion of a radiating section of the microwave antenna, an outer conductor and dielectric shielding. The inner conductor loops back around and toward the outer conductor of the coaxial cable feed such that a distal end of the inner conductor is operably disposed adjacent the dielectric shielding. The inner conductor includes one or more reactive components disposed thereon forming a reactively-loaded loop configuration.

The present disclosure provides a microwave antenna adapted to connect to a power source for performing a microwave ablation procedure. The microwave antenna includes a coaxial cable feed including an inner conductor defining a portion of a radiating section of the microwave antenna, an outer conductor and dielectric shielding. The inner conductor loops back around and toward the outer conductor of the coaxial cable feed such that a distal end of the inner conductor is operably disposed adjacent the dielectric shielding. The inner conductor includes one or more reactive components disposed thereon forming a reactively-loaded loop configuration.

BRIEF DESCRIPTION OF THE DRAWINGS

The above and other aspects, features, and advantages of the present disclosure will become more apparent in light of the following detailed description when taken in conjunction with the accompanying drawings in which:

FIG. 2A is partial, cut-away view of a distal tip of the microwave antenna depicted in FIG. 1B illustrating a radiating section associated with microwave antenna;

FIG. 2B is a cross-section view taken along line segment "2B-2B" illustrated in FIG. 2A;

DETAILED DESCRIPTION

Figure 1A:
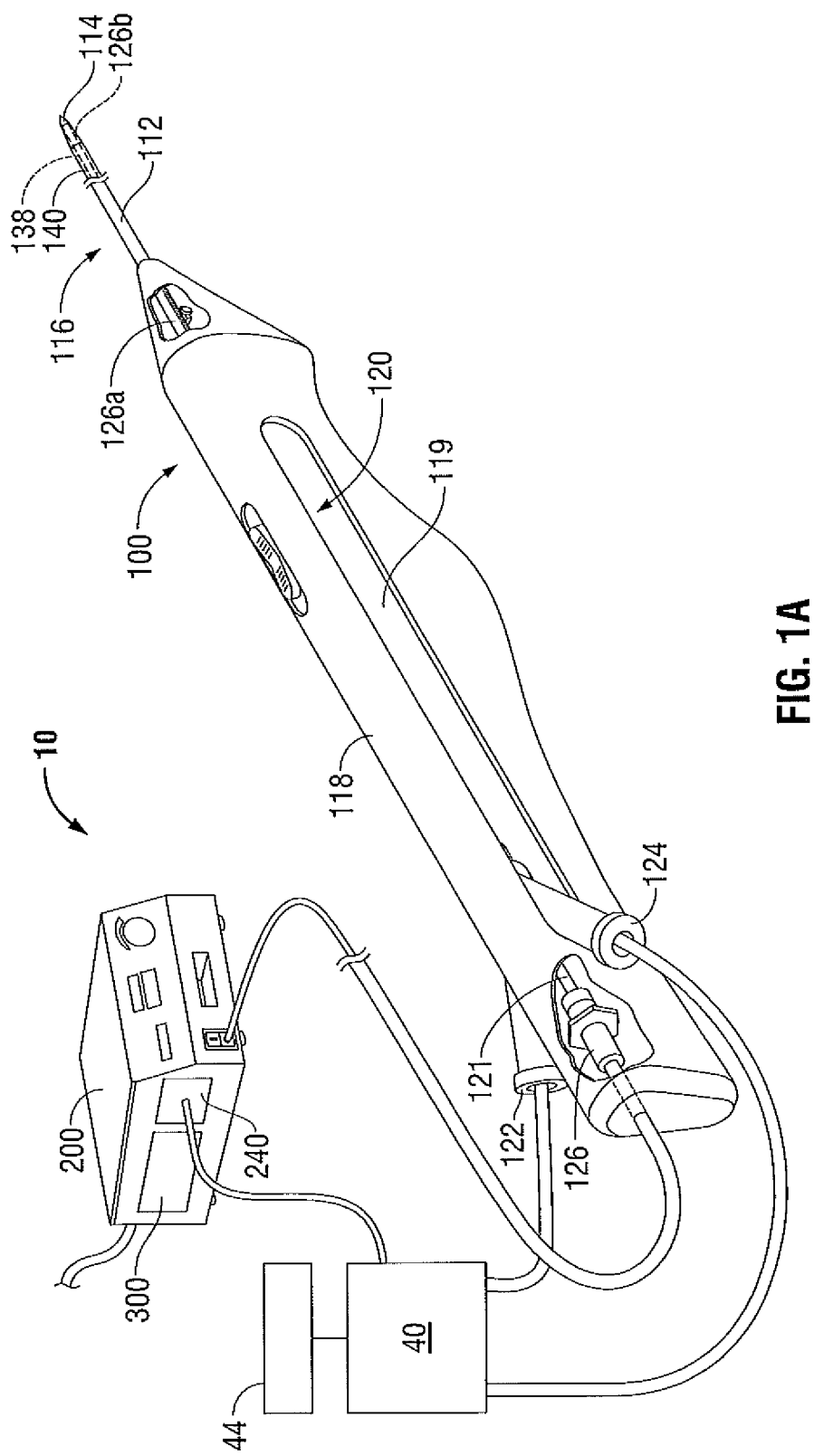
FIG. 1A is a perspective view of a microwave ablation system adapted for use with a microwave antenna that utilizes a reactively-loaded loop configuration according to an embodiment of the present disclosure.

Embodiments of the presently disclosed microwave antenna are described in detail with reference to the drawing figures wherein like reference numerals identify similar or identical elements. As used herein and as is traditional, the term "distal" refers to the portion which is furthest from the user and the term "proximal" refers to the portion that is closest to the user. In addition, terms such as "above", "below", "forward", "rearward", etc. refer to the orientation of the figures or the direction of components and are simply used for convenience of description.

Referring now to FIG. 1A, a microwave ablation system 10 adapted for use with a microwave antenna 100 that utilizes a reactively-loaded loop configuration according to an embodiment of the present disclosure is illustrated. The system 10 includes microwave antenna 100 that is adapted to connect to an electrosurgical power source, e.g., an RF and/or microwave (MW) generator 200 that includes or is in operative communication with one or more controllers 300 and, in some instances, a fluid supply pump 40. Briefly, microwave antenna 100 includes an introducer 116 having an elongated shaft 112 and a radiating or conductive tissue piercing tip 114 operably disposed within elongated shaft 112, a cooling assembly 120 having a cooling sheath 121, a handle 118, a cooling fluid supply 122 and a cooling fluid return 124, and an electrosurgical energy connector 126. Connector 126 is configured to connect the microwave antenna 100 to the electrosurgical power source 200, e.g., a generator or source of radio frequency energy and/or microwave energy, and supplies electrosurgical energy to the distal portion of the microwave antenna 100. Conductive tip 114 and elongated shaft 112 are in electrical communication with connector 126 via an internal coaxial cable 126a that extends from the proximal end of the microwave antenna 100 and includes an inner conductor 126b (shown in phantom) operably disposed within the shaft 112 and adjacent a radiating section 138 (shown in phantom) and/or the conductive or radiating tip 114. As is common in the art, the internal coaxial cable 126a includes a dielectric material and an outer conductor surrounding each of the inner conductor 126b and the dielectric material. A connection hub (not explicitly shown) disposed at a proximal end of the microwave antenna 100 operably couples connector 126 to internal coaxial cable 126a, and cooling fluid supply 122 and a cooling fluid return 124 to a cooling assembly 120. Radiating section 138 by way of conductive tip 114 (or in certain instances without conductive tip 114) is configured to deliver radio frequency energy (in either a bipolar or monopolar mode) or microwave energy to a target tissue site. Elongated shaft 112 and conductive tip 114 may be formed of suitable conductive material including, but not limited to copper, gold, silver or other conductive metals having similar conductivity values. Alternatively, elongated shaft 112 and/or conductive tip 114 may be constructed from stainless steel or may be plated with other materials, e.g., other conductive materials, such as gold or silver, to improve certain properties, e.g., to improve conductivity, decrease energy loss, etc. In an embodiment, the conductive tip 114 may be deployable from the elongated shaft 112.

Figure 1B:
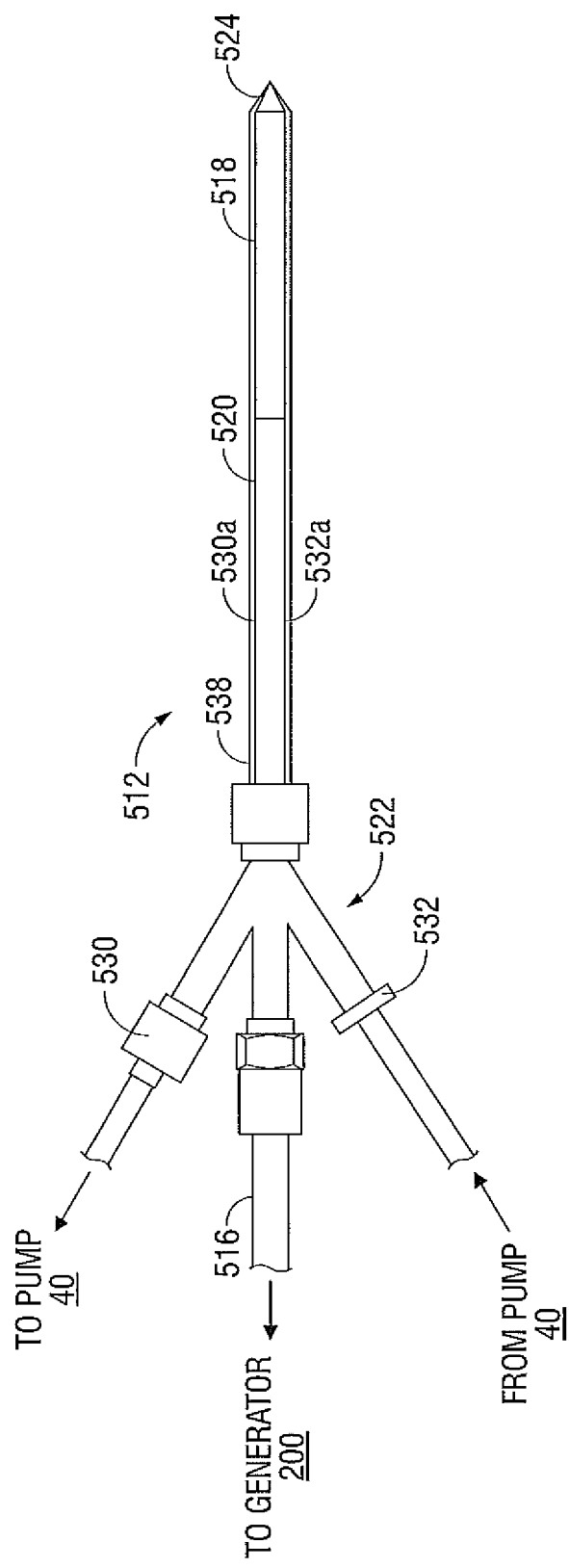
FIG. 1B is a perspective view of another type of microwave antenna that utilizes a reactively-loaded loop configuration according to an embodiment of the present disclosure and is adapted for use with the microwave ablation system depicted in FIG. 1A.

With reference now to FIG. 1B, a microwave antenna 512 that utilizes a reactively-loaded loop configuration according to an embodiment of the present disclosure and adapted for use with the microwave ablation system depicted in FIG. 1A is illustrated. Briefly, microwave antenna 512 operably couples to generator 200 including a controller 300 via a flexible coaxial cable 516. In this instance, generator 200 is configured to provide microwave energy at an operational frequency from about 300 MHz to about 10 GHz. Microwave antenna 512 includes a radiating section or portion 518 that may be connected by a feedline or shaft 520 to coaxial cable 516 that extends from the proximal end of the microwave antenna 512 and includes an inner conductor operably disposed within the shaft 520 and adjacent radiating section 518 and/or a conductive or radiating tissue piercing tip 524. More specifically, the microwave antenna 512 is coupled to the cable 516 through a connection hub 522. The connection hub 522 also includes an outlet fluid port 530 (similar to that of cooling fluid return 124) and an inlet fluid port 532 (similar to that of cooling fluid supply 122) that are connected in fluid communication with a sheath 538. The sheath 538 encloses the radiating portion 518 and the shaft 520 allowing for coolant fluid from the ports 530 and 532 to be supplied to and circulated around the antenna assembly 512 via respective fluid lumens 530a and 532a. The ports 530 and 532 may also couple to supply pump 40. For a more detailed description of the microwave antenna 512 and operative components associated therewith, reference is made to commonly-owned U.S. patent application Ser. No. 12/401,268 filed on Mar. 10, 2009.

With reference to FIG. 2A, a reactively-loaded loop configuration ("loop 400") according to an embodiment of the present disclosure is shown and designated 400. As defined herein, "reactively-loaded" is meant to mean including an element or component that opposes alternating current, caused by a build up of electric or magnetic fields in the element or component due to the current. Loop 400 may be operably associated with either of the radiating sections 138 or 518. For illustrative purposes loop 400 is described in terms of the radiating section 518 associated with the microwave antenna 512. Loop 400 is constructed by extending an inner conductor 516a, associated with the coaxial cable 516 distally past a dielectric material 516b and an outer conductor 516c. The inner conductor 516a is looped around and back toward the outer conductor 516c of the coaxial cable 516 such that a radiating section 518 having a generally "loop" like configuration is formed, the significance of which is described in greater detail below. In embodiments, loop 400 includes a diameter that ranges from about 3 mm to about 15 mm. Inner conductor 516a may have any suitable configuration including but not limited to wire, strip, etc. In the illustrated embodiments, inner conductor 516a includes a wire configuration having a diameter that ranges from about 0.0010 inches to about 0.0020 inches. In the instance where the inner conductor 516a includes a strip configuration, the strip may include a width that ranges from about 0.0010 inches to about 0.0020 inches. To optimize electrosurgical energy transfer from the generator 200 to the microwave antenna 512 it is important that an impedance match be present between coaxial cable 516, radiating section 518 and tissue at a target tissue site. In accordance with the present disclosure, a length of the loop 400 is configured for tuning, i.e., impedance matching, an impedance associated with the inner conductor 516a, microwave antenna 512 and tissue at a target tissue site such that optimal transfer of electrosurgical energy is provided from the generator 200 to the radiating section 518 such that a desired tissue effect is achieved at a target tissue site.

With continued reference to FIG. 2A, one or more reactive elements or components are operably disposed along a length of loop 400 associated with the inner conductor 516a to achieve a desired electrical effect at the radiating section 518. In the embodiment illustrated in FIG. 2A, one or more coiled sections 402 (one coiled section is shown for illustrative purposes) that serves as an inductive component is formed (or in some instances positioned, such as, for example, when an inductive component is utilized) adjacent a proximal end of the inner conductor 516a. The coiled section 402 may include any number of suitable turns such that a desired voltage may be induced therein by an electromagnetic field present in the coiled section 402 when electrosurgical energy is transmitted to the microwave antenna 512 and, more particularly, to the radiating section 518. One or more capacitive components 404 (three capacitive components are shown for illustrative purposes) are operably disposed at distal end of the loop 400 and/or inner conductor 516a. More particularly, capacitive components 404 are positioned adjacent outer conductor 516c and/or dielectric material 516b. The capacitive components 404 are in the form of three capacitor disks 404 that function to provide a capacitive effect at the distal end of the loop 400 when the distal end of the loop 400 is positioned adjacent (or contacts) the outer conductor 516c and/or the dielectric material 516b. The inductive and capacitive components 402 and 404, respectively, may be arranged in any suitable electrical configuration, i.e., series or parallel.

In the embodiment illustrated in FIG. 2A, the inductive and capacitive components 402 and 404, respectively, are arranged in series with respect to each other. In an alternate embodiment, the respective inductive and capacitive components 402 and 404 may be arranged in a parallel configuration with respect to each other. That is, inner conductor 516a may be split into two branches forming a parallel configuration, wherein each branch includes a respective reactive component. More particularly, one branch may include one or more inductive components 402 and one branch may include one or more capacitive component 404. To achieve desired capacitive or inductive effects at the loop 400 formed by the inner conductor 516a, a thickness of the inner conductor 516a may varied (i.e., increased or decreased) as needed. Loading the loop 400 with one or more reactive components described herein enables the radiating section 518 to be shortened or lengthened during the manufacturing process such that a desired electrical effect (e.g., impedance) or output may be achieved at the radiating section 518 and/or conductive tip 524. Additionally, reactive loading of the loop 400 allows for miniaturization of the radiating section 518, which, in turn, provides for a more practical invasive microwave antenna 512 and/or radiating section 518.

Figure 3:
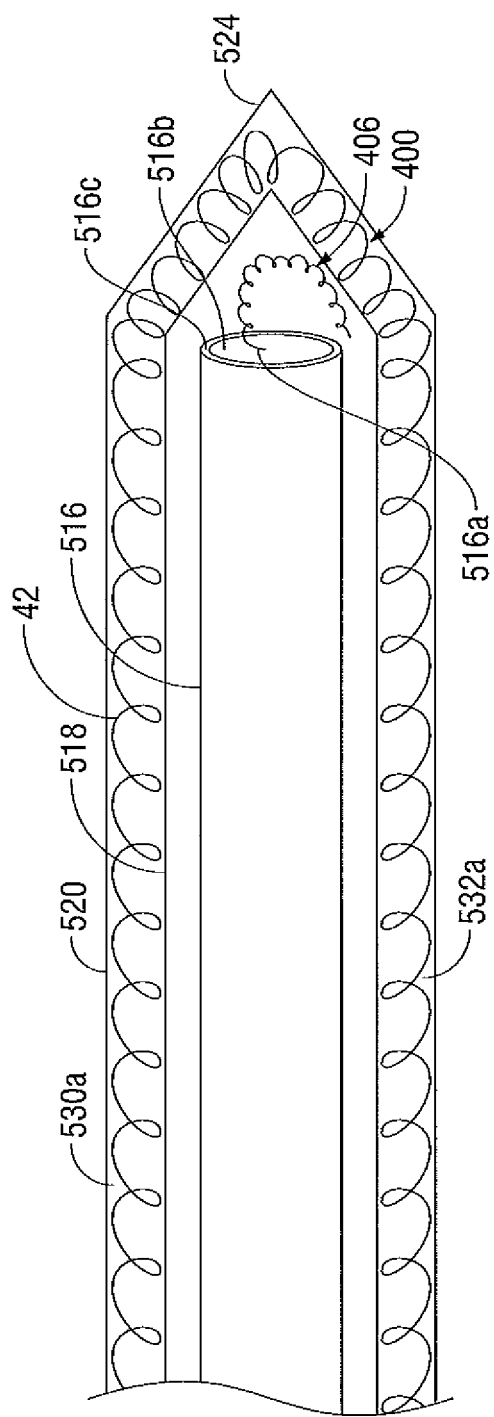
FIG. 3 is partial, cut-away view of the distal tip of the microwave antenna depicted in FIG. 1B illustrating an alternate embodiment of the radiating section depicted in FIG. 2A.

In an alternate embodiment, see FIG. 3, the loop 400 may include a spiral loop configuration. In this instance, the loop 400 includes one or more spiral sections 406 that provide one or more reactive effects, e.g., an inductive effect described above. Not unlike the loop 400 illustrated in FIG. 2A, a distal end of the spiral section 406 of loop 400 and/or the inner conductor 516a is positioned adjacent (or contacts) the outer conductor 516c and/or the dielectric material 516b. While not explicitly shown, it is within the purview of the present disclosure that one or more of the reactive components described above, e.g., an inductive component 402 and/or a capacitive component 404, may be operably disposed within the electrical path of the spiral section 406 of the loop 400. That is, the inductive component 402 and/or a capacitive component 404 may be arranged in series or parallel configurations with respect to each other and/or the spiral section 406 of loop 400.

Figure 4:
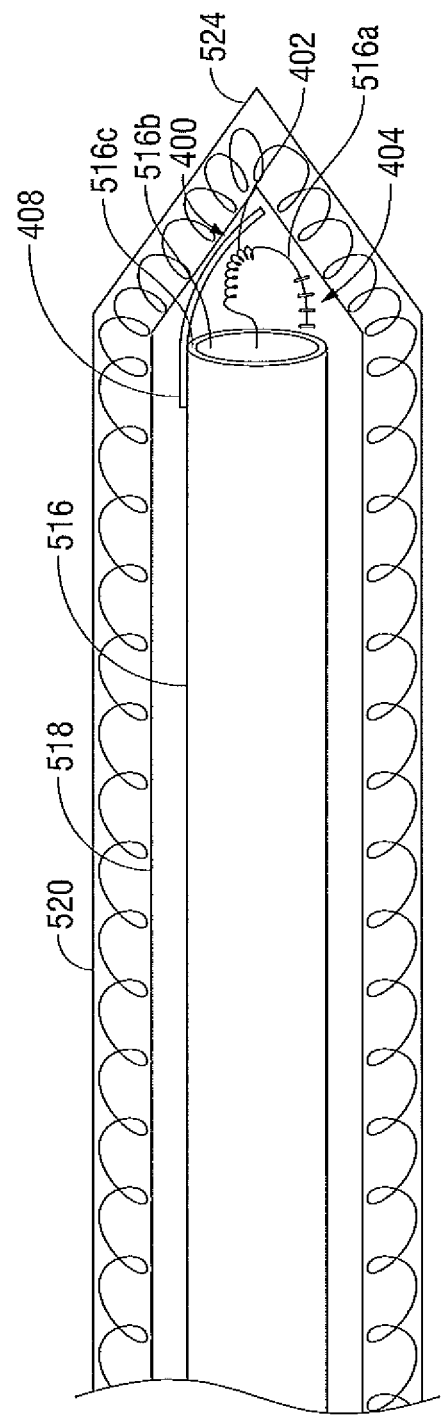
FIG. 4 is partial, cut-away view of the distal tip of the microwave antenna depicted in FIG. 1B illustrating a conductive shield operably positioned adjacent the radiating section depicted in FIG. 2A.

In one particular embodiment, one or more structure(s) or device(s) may be employed to concentrate the electrosurgical energy radiating from the radiating section 518 and/or conductive tip 524 to tissue at a target tissue site. More particularly, and with reference to FIG. 4, a reflector or shield 408 may be operably positioned adjacent and partially wrapped (or in some instances substantially wrapped) around the loop 400, e.g., configuration of loop 400 illustrated in FIG. 2A (or other suitable configuration of loop 400). More particularly, the shield 408 is operably secured to and disposed at a distal end of the coaxial cable 516 adjacent the loop 400. Shield 408 may be secured to coaxial cable 516 by any suitable securement methods including but not limited to soldering, brazing, welding, adhesives, etc. In the illustrated embodiments, shield 408 is secured to coaxial cable 516 by way of brazing. In certain embodiments, shield 408 may be monolithically formed with the radiating section 518. In another embodiment, shield 408 may be grounded or secured to an internal portion of the shaft 520 of the microwave antenna 512. Shield 408 may be made from any suitable material including but not limited to materials that are conductive, non-conductive or partially conductive. More particularly, shield 408 may be made from metal, metal alloys, plastic, ceramic, etc. In one particular embodiment, shield 408 is made from metal, such as, for example, a metal selected from the group consisting of copper, silver, gold, platinum, stainless steel and titanium.

Figure 5:
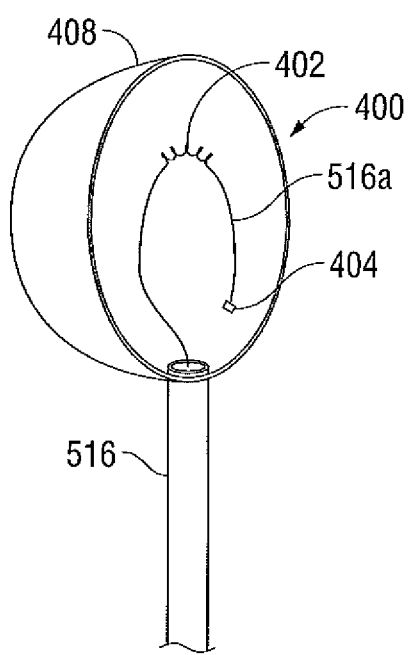
FIG. 5 is partial, cut-away view of the distal tip of the microwave antenna depicted in FIG. 1B illustrating a conductive shield operably positioned adjacent the radiating section depicted in FIG. 2A according to an alternate embodiment of the present disclosure.
Figure 6:
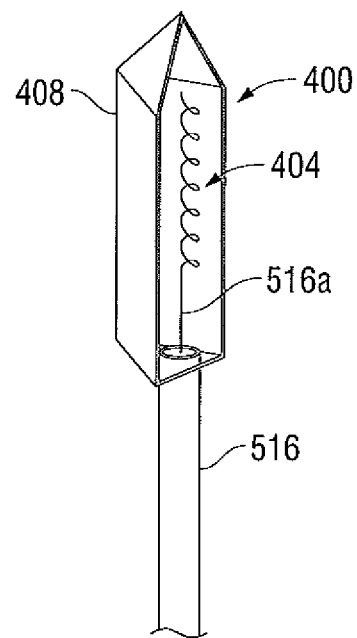
FIG. 6 is partial cut-away view of the distal tip of the microwave antenna depicted in FIG. 1B illustrating a conductive shield operably positioned adjacent the radiating section depicted in FIG. 2A according to another embodiment of the present disclosure.

Shield 408 is configured to provide enhanced directionality of the radiating pattern of the electrosurgical energy transmitted to the radiating section 518 and/or conductive tip 524. In one particular embodiment, the shield 408 may include a generally hemispherical or clamshell configuration (FIG. 5). In another embodiment, the shield 408 may be elongated having a generally triangular cross-section configuration (FIG. 6). In either instance, the shield 408 concentrates and/or directs the electrosurgical energy transmitted to the radiating section 518 and/or conductive tip 524 to the target tissue site. Examples of other suitable types of reflectors or shields (and operative components associated therewith) are described in commonly-owned U.S. patent application Ser. Nos. 12/542,348 and 12/568,524 filed on Aug. 17, 2009 and Sep. 28, 2009, respectively.

In the embodiment illustrated in FIG. 1A, the generator is shown operably coupled to fluid supply pump 40. The supply pump 40 is, in turn, operably coupled to a supply tank 44. In embodiments, the supply pump 40 is operatively disposed on the generator 200, which allows the generator to control the output of a cooling fluid 42 from the supply pump 40 to the microwave antenna 512 according to either open and/or closed control loop schemes. As can be appreciated providing the cooling fluid 42 (see FIGS. 2A and 3) to the radiating section 518 and/or the loop 400 increases the power handling capability of the microwave antenna.

As noted above, in some instances it may prove useful to utilize a microwave antenna (e.g., microwave antenna 100) that includes a deployable tip 114. In this instance, the deployable conductive tip 114 includes a configuration of loop 400 proportioned small enough in diameter to facilitate deployment of the conductive tip 114. During a surgical procedure, e.g., ablation procedure, a portion of the loop 400 may be positioned around a tumor or soft tissue.

In certain embodiments, a portion of the microwave antenna may be coated with a non-stick material 140 (see FIG. 1A, for example), such as, for example, polytetrafluoroethylene, commonly referred to and sold under the trademark TEFLON® owned by DuPont™.

In certain embodiments, a dielectric material 517 (see FIG. 2A, for example) may surround the radiating section 518 and/or the loop 400 and reactive components associated therewith to achieve an impedance match between the microwave antenna 100 and tissue to emit a radiating pattern from the radiating section 518 of the microwave antenna 512.

Operation of system 10 is now described with respect to FIGS. 1B and 2. A portion of the microwave antenna, e.g., a radiating section 518 and/or conductive tip 524, is positioned adjacent tissue at a target tissue site (or in some instances, a portion of the microwave antenna 512, e.g., a portion of loop 400, may be wrapped around tissue, e.g., a tumor). In certain instances, a fluid 42 may be circulated through the fluid lumens 530a and 532a and around the radiating section 518, see FIG. 2A, for example. Thereafter, electrosurgical energy is transmitted from the generator 200 to the radiating section 518 and/or conductive tip 524 of the microwave antenna 512 such that a desired tissue effect may be achieved at the target tissue site. In accordance with the present disclosure, the loop 400 improves electrosurgical energy transfer from the generator 200 to the microwave antenna 512 and/or the target tissue site and allows the microwave antenna 512 or portion associated therewith, e.g., radiating section 518 and/or conductive portion 524, to be utilized with more invasive ablation procedures.

From the foregoing and with reference to the various figure drawings, those skilled in the art will appreciate that certain modifications can also be made to the present disclosure without departing from the scope of the same. For example, one or more modules associated with the generator 200 and/or controller 300 may be configured to monitor the reactive elements or components, e.g., inductive element 402, associated with the loop 400 such that a specific electromagnetic field is generated by the reactive elements or components during the transmission of electrosurgical energy from the generator 200 to the microwave antenna 512. More particularly, one or more sensors (e.g., one or more voltage and current sensors) may be operably positioned at a predetermined location and adjacent the radiating section 518 and/or loop 400. More particularly, the sensor(s) may be operably disposed along a length of the loop 400 and in operative communication with the module(s) associated with the generator 200 and/or controller 300. The sensor(s) may react to voltage and/or current fluctuations associated with the loop 400 and caused by electromagnetic fields fluctuations generated by one or more of the reactive components, e.g., inductive element 402, associated with the loop 400. In this instance, the sensor(s) may be configured to trigger a control signal to the module(s) when an electromagnetic field of predetermined strength is generated. When the module(s) detects a control signal, the module may send a command signal to the generator 200 and/or controller 300 such that the electrosurgical power output to the microwave antenna 512 may be adjusted accordingly.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A microwave ablation system, comprising:
    a power source;
    a microwave antenna;
    a coaxial cable feed adapted to connect the microwave antenna to the power source, the coaxial cable feed including an inner conductor, an outer conductor, a dielectric shielding, and a radiating section;
    a reactively-loaded loop structure coupled to the inner conductor, the reactively-loaded loop structure having at least two reactive components; and
    a conductive shield disposed adjacent a distal end of the radiating section and extending beyond the distal end of the radiating section to at least partially wrap around the radiating section.

2. The microwave ablation system according to claim 1, wherein the inner conductor defines at least a portion of the radiating section.

3. The microwave ablation system according to claim 1, wherein at least one of the at least two reactive components is selected from the group consisting of an inductor, a capacitor, and combinations thereof.

4. The microwave ablation system according to claim 3, wherein the inner conductor includes a combination of at least one inductor and at least one capacitor.

5. The microwave ablation system according to claim 4, wherein the at least one inductor and the at least one capacitor are disposed on the inner conductor in series with respect to each other.

6. The microwave ablation system according to claim 1, wherein the inner conductor includes a spiral configuration and capacitively couples a distal end of the inner conductor to the dielectric shielding.

7. The microwave ablation system according to claim 1, wherein a dielectric material surrounds the radiating section and at least one of the at least two reactive components, the dielectric material providing an impedance match between the microwave antenna and tissue.

8. A microwave antenna, comprising:
    a coaxial cable feed including an inner conductor, an outer conductor, a dielectric shielding, and a radiating section;
    a reactively-loaded loop structure coupled to the inner conductor, the reactively-loaded loop structure having at least two reactive components; and
    a conductive shield disposed adjacent a distal end of the radiating section and extending beyond the distal end of the radiating section to at least partially wrap around the radiating section.

9. The microwave antenna according to claim 8, wherein the inner conductor defines at least a portion of the radiating section.

10. The microwave antenna according to claim 8, wherein at least one of the at least two reactive components is selected from the group consisting of an inductor, a capacitor, and combinations thereof.

11. The microwave antenna according to claim 10, wherein the inner conductor includes a combination of at least one inductor and at least one capacitor.

12. The microwave antenna according to claim 11, wherein the at least one inductor and the at least one capacitor are disposed on the inner conductor in series with respect to each other.

13. The microwave antenna according to claim 8, wherein the inner conductor includes a spiral configuration and capacitively couples a distal end of the inner conductor to the dielectric shielding.

14. The microwave antenna according to claim 8, wherein a dielectric material surrounds the radiating section and at least one of the at least two reactive components, the dielectric material providing an impedance match between the microwave antenna and tissue.

* * * * *